US012678663B2

(12) United States Patent
Bhushan et al.

(10) Patent No.: US 12,678,663 B2
(45) Date of Patent: Jul. 14, 2026

(54) METHOD AND SYSTEM FOR ISCHEMIC PRE-CONDITIONING USING EXERCISE

(71) Applicant: FOURTH FRONTIER TECHNOLOGIES, Pvt. Ltd., Bangalore (IN)

(72) Inventors: Manav Bhushan, Bangalore (IN); Sandeep Sibal, Bangalore (IN)

(73) Assignee: FOURTH FRONTIER TECHNOLOGIES, PVT. LTD, Karnataka (IN)

( * ) Notice: Subject to any disclaimer, the term of this patent is extended or adjusted under 35 U.S.C. 154(b) by 134 days.

(21) Appl. No.: 17/381,395

(22) Filed: Jul. 21, 2021

(65) Prior Publication Data

US 2023/0022981 A1     Jan. 26, 2023

(51) Int. Cl.
| | |
|---|---|
| *A63B 24/00* | (2006.01) |
| *A61B 5/00* | (2006.01) |
| *A61B 5/0205* | (2006.01) |
| *A61B 5/358* | (2021.01) |
| *A63B 71/06* | (2006.01) |

(52) U.S. Cl.
CPC ........ *A63B 24/0062* (2013.01); *A61B 5/0002* (2013.01); *A61B 5/0205* (2013.01); *A61B 5/358* (2021.01); *A61B 5/6823* (2013.01); *A61B 5/6831* (2013.01); *A61B 5/6832* (2013.01); *A61B 5/7405* (2013.01); *A61B 5/742* (2013.01); *A61B 5/7455* (2013.01); *A61B 5/746* (2013.01); *A63B 71/0622* (2013.01); *A63B 71/0686* (2013.01); *A61B 2562/0219* (2013.01); *A63B 2071/0625* (2013.01); *A63B 2071/0655* (2013.01); *A63B 2220/05* (2013.01); *A63B 2220/807* (2013.01); *A63B 2220/836* (2013.01);

(Continued)

(58) Field of Classification Search
CPC ........ A63B 24/0062; A63B 2071/0625; A63B 2071/0655; A63B 71/0622; A63B 71/0686; A63B 2225/74; A61B 5/358; A61B 5/0002; A61B 5/0205; A61B 5/6823; A61B 5/6831; A61B 5/6832; A61B 5/7405; A61B 5/742; A61B 5/7455; A61B 5/746; A61B 2562/0219
USPC ....................................................... 600/301
See application file for complete search history.

(56) References Cited

U.S. PATENT DOCUMENTS

| | | | | | |
|---|---|---|---|---|---|
| 9,801,562 | B1 * | 10/2017 | Host-Madsen | ........ | A61B 5/349 |
| 10,206,572 | B1 * | 2/2019 | Utley | .................. | A61B 5/0022 |

(Continued)

FOREIGN PATENT DOCUMENTS

| | | | | | |
|---|---|---|---|---|---|
| WO | WO-2004052192 A1 * | 6/2004 | | ............. | A61B 5/685 |

*Primary Examiner* — Michael J Lau
(74) *Attorney, Agent, or Firm* — Dickinson Wright PLLC

(57) ABSTRACT

The various embodiments of the present invention provide a system and method for a fully mobile, non-invasive, continuous system for monitoring the cardiovascular and musculoskeletal health of an individual during exercise, and for administering a protocol for ischemic pre-conditioning. The system includes a wearable devices affixed on the user with a chest strap, coupled with an application running on a computing device (smartphone/smartwatch), which performs various computations on the wearable device, and allows the user to get real time alerts during exercise, by way of vibrations or audio messages or notifications on the gateway device, to guide them through a protocol for ischemic pre-conditioning.

30 Claims, 3 Drawing Sheets

Schematic layout of the system comprising of the wearable device and mobile application

(52) U.S. Cl.
CPC ....... *A63B 2225/50* (2013.01); *A63B 2225/74*
(2020.08)

(56)                   References Cited

U.S. PATENT DOCUMENTS

| | | | |
|---|---|---|---|
| 2004/0073098 A1* | 4/2004 | Geva ................... | A61B 5/7267 |
| | | | 600/300 |
| 2004/0230105 A1* | 11/2004 | Geva ..................... | A61B 5/316 |
| | | | 600/509 |
| 2009/0171228 A1* | 7/2009 | Fischell ................ | A61B 5/287 |
| | | | 600/517 |
| 2013/0171599 A1* | 7/2013 | Bleich ............... | A63B 24/0062 |
| | | | 434/247 |
| 2015/0149940 A1* | 5/2015 | Kaiser ................... | G16H 50/30 |
| | | | 715/765 |
| 2016/0331257 A1* | 11/2016 | Baumann ............ | A61B 5/6833 |
| 2018/0358119 A1* | 12/2018 | Bhushan ............... | G16H 40/63 |

* cited by examiner

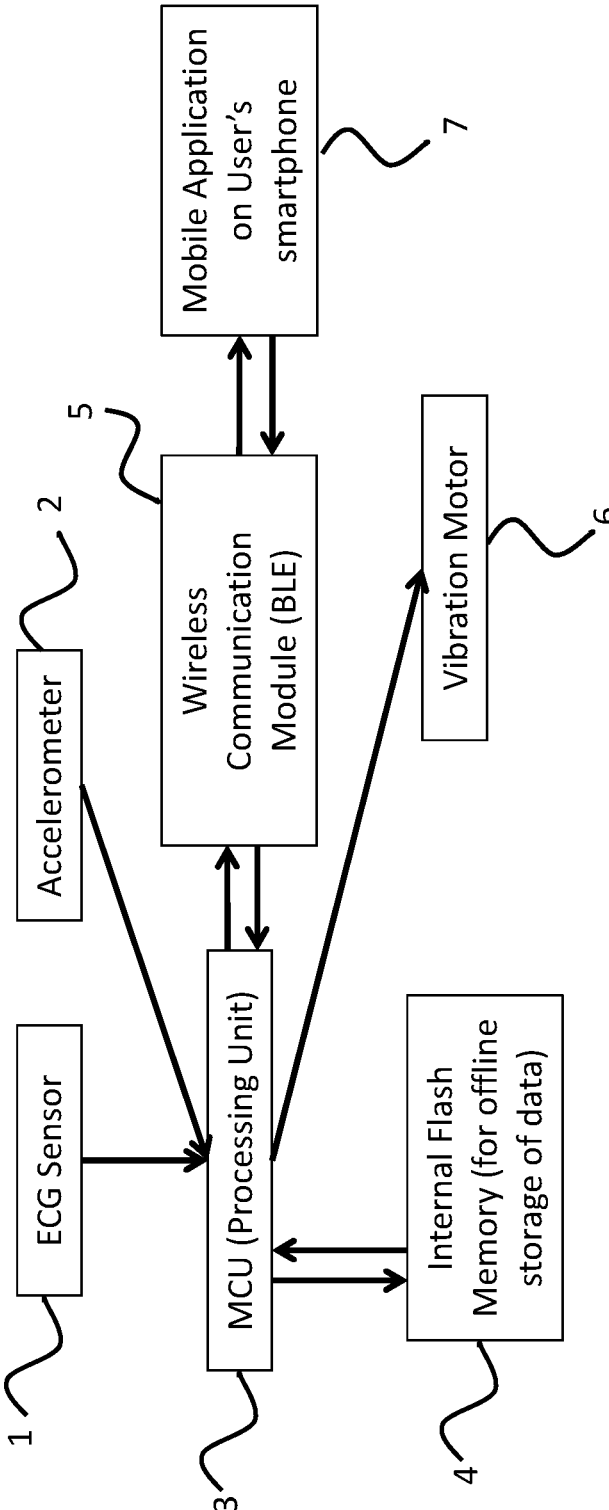
Fig 1: Schematic layout of the system comprising of the wearable device and mobile application

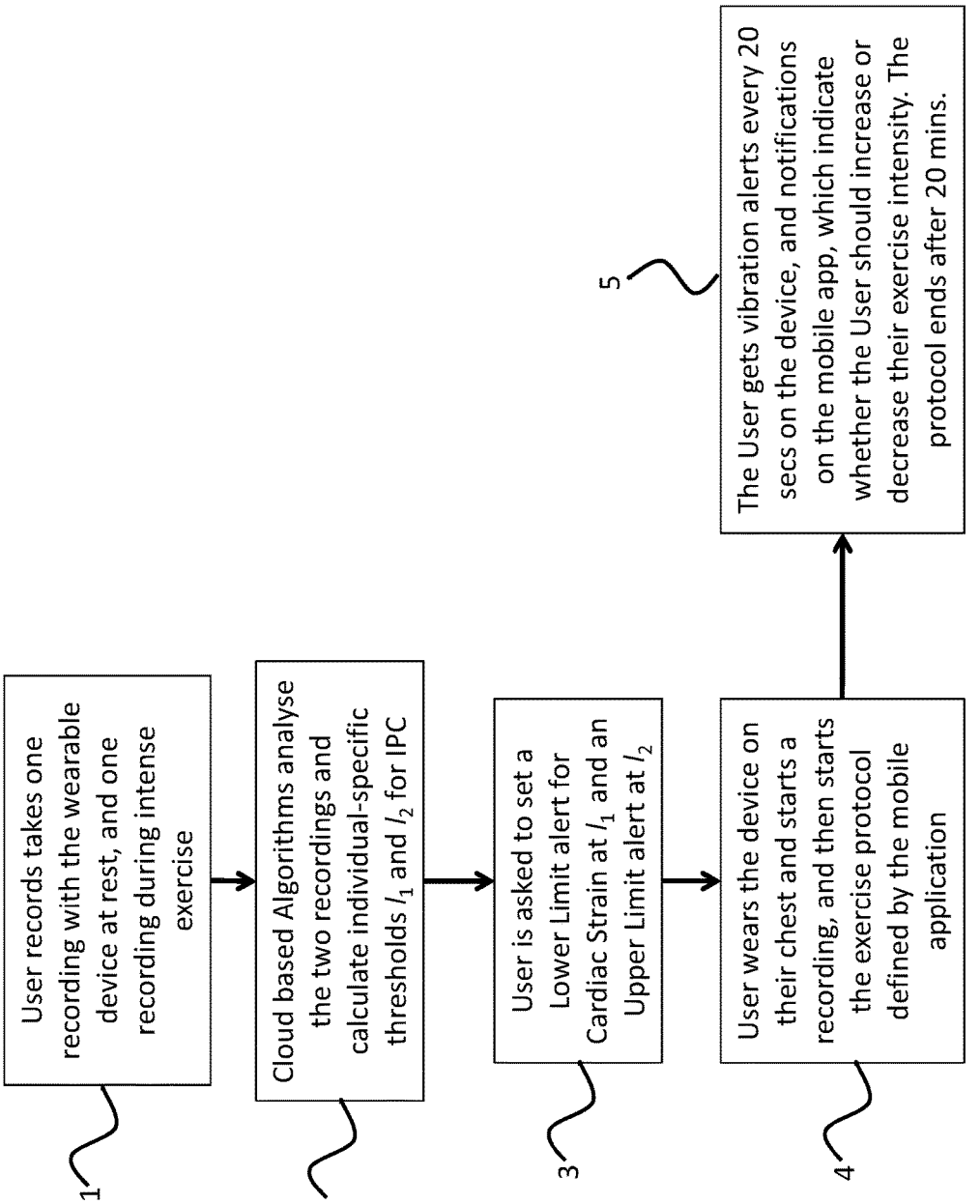
Fig 2: Process flowchart for starting the protocol for Ischemic Preconditioning

Figure 3:
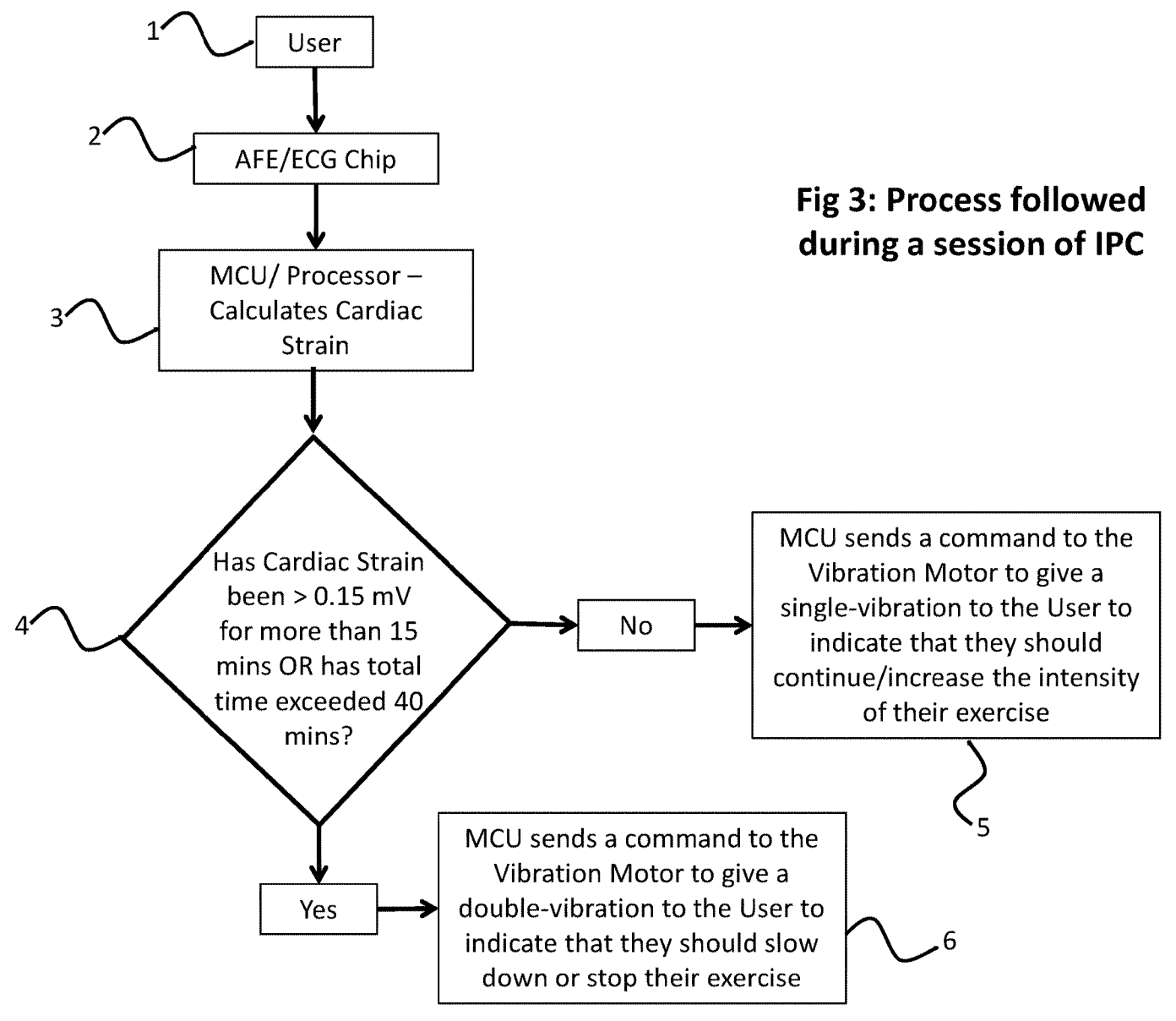

Fig 3: Process followed during a session of IPC

User — 1

AFE/ECG Chip — 2

MCU/ Processor – Calculates Cardiac Strain — 3

Has Cardiac Strain been > 0.15 mV for more than 15 mins OR has total time exceeded 40 mins? — 4

No

Yes

MCU sends a command to the Vibration Motor to give a single-vibration to the User to indicate that they should continue/increase the intensity of their exercise — 5

MCU sends a command to the Vibration Motor to give a double-vibration to the User to indicate that they should slow down or stop their exercise — 6

METHOD AND SYSTEM FOR ISCHEMIC PRE-CONDITIONING USING EXERCISE

BACKGROUND

The present invention is generally related to health monitoring devices. The present invention is particularly related to a device and system for monitoring and improving cardiovascular health. The present invention is more particularly related to cardiovascular health monitoring, and a protocol for providing ischemic pre-conditioning (IPC) using measurement and real-time alerts from wearable devices, in order to improve the user's cardiovascular health.

RELATED ART

U.S. Pat. Pub. No. 2015/0099945 A1 describes an activity monitoring device (AMD) that measures Heart Rate, running style, cadence, biking posture, etc.

U.S. Pat. Pub. No. 2015/0099945 A1 (Wahoo) describes an activity monitoring device (AMD) that measures Heart Rate, running speed, ground contact time, vertical oscillation, cadence, biking posture, etc.

U.S. Pat. No. 9,699,859 B1 (Moov) discloses an automated fitness coaching device, comprising light-emitting diodes (LEDs) and multiple sensors, giving guidance through audio messages delivered through the phone to improve running styles.

U.S. Pat. Pub. No. US2013/0178958 A1 (Garmin) discloses a system comprising of an inertial sensor coupled to the User's torso, measuring speed, cadence, time energy cost, distance energy cost and acceleration energy cost.

U.S. Pat. No. 8,630,867 B2 discloses a system and method for remote diagnosis using a wearable device. The patent also discloses a system and method for a user to communicate with a number of doctors/specialists through the wearable device which is paired with a computing device such as a Smartphone.

U.S. Pat. No. 8,107,920 B2 discloses a wearable health monitoring system. According to this patent, one or more concerned personnel are alerted when a user's condition is critical and is below a set threshold. The patent also teaches measuring parameters such as heart rate, respiration rate, and the like using sensors available on the wearable device.

U.S. Pat. No. 8,790,266 B2 discloses a system for remote ischemic preconditioning that includes a cuff, and actuator, and a controller that operates the actuator.

U.S. Pat. No. 8,911,469 B2 discloses a method of optimal remote ischemic preconditioning (ORIP) by utilizing a pair of programmable pneumatic cuffs that inflate/deflate alternately occluding blood circulation to each of the limbs for pre-defined time intervals, according to a treatment protocol. The treatment protocol includes a plurality of treatment cycles that each comprise cuff actuation, an ischemic duration, cuff release, and a reperfusion duration.

However, in order to monitor health parameters in a mobile setting such as during a long-distance run or other exercise, there is a need for a wearable device affixable to the body for long periods of time and configured to continuously monitor of various health parameters, particularly cardiac health parameters. It is desirable that such a device would compute health parameters locally based on datastreams from various sensors and alert the user when a computed health parameter is outside of a normal range. Moreover, the capability to transmit the health parameters to a smartphone or other gateway device and to store the health data remotely for analysis by health professionals is also desired.

SUMMARY

The various embodiments of the present invention provide a system and method for monitoring and improvement of cardiovascular health for the User using specific exercise protocols governed by real-time feedback received from a wearable device.

The system includes a wearable device that is coupled with a chest strap, which allows the device to be attached to the body of the User. The wearable device includes a plurality of electrodes, an electronic circuitry to measure electric potentials for one or more channels, and/or a circuitry for measuring electrical impedance on the skin using electrodes, and/or one or more accelerometers. This wearable device communicates with a mobile application and provides tactile feedback to the User, to guide them through a protocol for ischemic pre-conditioning.

The system is designed to measure the ST-segment deviation from the ECG signal that is recorded on the primary wearable device, and alert the User through a vibration motor included in the wearable device and/or with visual or auditory feedback given through the mobile application, when the User's ST-depression value is crossing a certain predefined threshold. The system is designed to guide the User to exercise in a way such that they stay in a certain zone of ST-depression values for a certain amount of time, and are warned if they exceed the upper limit of this pre-defined zone.

The various embodiments of the present invention provide a system wherein a wearable device capable of monitoring various physiological signals also has a processor capable of recording data to a memory chip on the device, and computing different metrics, without the need for any external device. The device is further capable of sending alerts to the User by way of LEDs situated on the device, and/or an electronic display, and/or a vibration motor, and/or an audio speaker located on the device.

The various embodiments of the present invention provide a system that includes a wearable device located on the torso of the User, which includes a wireless communication module (Bluetooth and/or WiFi and/or NFC) capable of communicating raw data and various metrics computed on the wearable device to a gateway device such as a smartphone or a smartwatch.

The various embodiments of the present invention provide systems and methods for monitoring and analysing bio-signals measured by one or more wearable devices, and alerting the user in real-time, during exercise when certain conditions are detected, and thereby guiding the User through a protocol for ischemic preconditioning (IPC).

These and other aspects of the embodiments herein will be better appreciated and understood when considered in conjunction with the following description and the accompanying drawings. It should be understood, however, that the following descriptions, while indicating the preferred embodiments and numerous specific details thereof, are given by way of an illustration and not of a limitation. Many changes and modifications may be made within the scope of the embodiments herein without departing from the spirit thereof, and the embodiments herein include all such modifications.

The other objects, features, and advantages will occur to those skilled in the art from the following description of the preferred embodiment and the accompanying drawings.

BRIEF DESCRIPTION OF THE DRAWINGS

FIG. 1 shows a schematic layout of the system comprising of the wearable device and mobile application.

FIG. 2 shows a Process flowchart for starting the protocol for Ischemic Preconditioning.

FIG. 3 shows a flowchart for the process followed during a session of IPC.

DETAILED DESCRIPTION

In the following detailed description, a reference is made to the accompanying drawings that form a part hereof, and in which the specific embodiments that may be practiced is shown by way of illustration. These embodiments are described in sufficient detail to enable those skilled in the art to practice the embodiments and it is to be understood that the logical, mechanical and other changes may be made without departing from the scope of the embodiments. The following detailed description is therefore not to be taken in a limiting sense.

The various embodiments of the present invention provide a system and method for monitoring the health of a user continuously during exercise, and providing feedback to guide the user through a protocol for ischemic preconditioning (IPC). The system comprises of a wearable device or devices which communicate wirelessly to a gateway device such as a smartphone/smartwatch/router.

The wearable device(s) comprise of an electronic module or a component that is reusable and rechargeable (via a wire, such as a micro-USB/firewire/Pogo pins or wirelessly or both) or disposable and non-rechargeable, and is affixed to the body of the User with the help of a one-sided or two-sided adhesive, or with a strap, or a clip which ensures contact between the wearable device and the User's torso.

In various embodiments, the Wearable comprises of the following elements: two or more electrodes connected to a single analog front end (AFE) system, which may further transmit the signal to an analog-to-digital converter (ADC) and then on to an MCU. The Wearable device may also contain a digital PPG sensor and/or one or more accelerometers and/or a temperature sensor configured for measuring the skin temperature, at the location where the device is affixed to the body.

In various embodiments, the electrodes, AFE and MCU together measure and record electrical signals comprising of the Electrocardiogram (ECG) when stuck on the chest.

In various embodiments, the system includes a strap with two or more electrodes, and a device with two or more electrodes, which couples with the strap. The strap may include one or more energy harvesting chips that can harvest energy from the temperature difference between the User's skin and the ambient environment.

In various embodiments, the strap may also include various sensors including one or more of the following: a temperature sensor, a PPG sensor, an array of electrodes to measure ECG and/or skin conductance. This strap may couple with a device containing a wireless communication module, a microprocessor, and/or an accelerometer and other sensors.

In various embodiments, the Wearable device may be affixed to the skin of the User with the help of an adjustable or elastic band that fits around the User's torso, and which has a marking or cavity that holds the Wearable device in a particular desired location.

In various embodiments, the Wearable device may be placed in a cavity or specially designed appendage that is part of any article of clothing, such as a shirt or vest or harness that is in contact with some part of the Users chest. This piece of clothing would keep the Wearable device in a particular location on the User's chest.

In various embodiments, the Wearable device is fabricated upon a flexible printed circuit board (PCB), or on one or more hard PCBs connected with flexible PCBs (together making up a rigid-flex PCB), or on any combination of flexible or hard PCBs. According to an embodiment of the present invention, the width of the wearable device is 5-250 mm in length, 3-250 mm in width, and 1-250 mm in height, and adapts to almost any surface on the body including the abdomen or chest of the user.

In various embodiments, the Wearable device includes a vibration motor to alert the user under certain pre-defined circumstances. Alerts are sent when some abnormality is detected from the bio-signals being recorded—either as computed on a Multipoint Control Unit (MCU) itself in real-time, or as computed on the web server on the cloud and then communicated to the Wearable by way of Bluetooth of some other wireless communication protocol, or according to the findings of a doctor looking at the database on the web client communicated to the Wearable by way of Bluetooth of some other wireless communication protocol.

In various embodiments, the Wearable device includes one or more LEDs, visible through the casing, or placed on top of the casing, which communicates different information about the device status and functionality to the user, and/or a microprocessor or other processor to collect data from the multiple sensors, and perform different kinds of algorithms on the wearable device itself.

In various embodiments, the Wearable device includes an integrated circuit (IC) for wireless data communication, that enables it to connect and communicate and send and receive data from a smartphone/smartwatch or another gateway device. Further, the Wearable device may include a memory chip that allows it to store data for long periods of time, and then to communicate this saved data to other locations.

In various embodiments, the Wearable device contains an audio speaker that allows the User to hear certain alerts or audio commands. The Wearable device may also contain an audio recorder that allows the User to record or send audio instructions to the Wearable.

In various embodiments, the wearable device may be re-charged through a wired connection, such as a micro-USB connection/firewire/pogo pin, or through a wireless charger, and hence can be reused many times. Further, the Wearable device may have a casing which is waterproof, and may therefore be used in conditions where there are water and rain, or under water.

In various embodiments, the wearable device includes a gyroscope, which can calculate the exact orientation of the User while he/she is wearing the device on any part of the body. The gyroscope sends the data of the User's orientation to the computing device included in the wearable, and the User can be alerted when the orientation is falling outside a certain prescribed range, or when it changes more rapidly than a prescribed rate of change.

In various embodiments, the wearable device includes a magnetometer, which can calculate the orientation of the User with respect to the Earth's magnetic field, and provide a measurement for the direction in which the User is running/walking.

In various embodiments, the Wearable device includes one or more accelerometers capable of measuring acceleration within a range of 0.01 milliG-20 G, and hence capable of measuring steps, breathing, heartbeats, opening and closing of heartvalves (the aortic and mitral valves), rapid ejection and rapid filling, when placed at different locations on the body. The accelerometer(s) record Seismocardiography (SCG) when affixed to particular parts of the User's chest. The accelerometers may also include a tap-detection functionality, which allow the user to activate different kinds of processes with a single/double tap.

In various embodiments, the Wearable device includes a reflective Photoplethysmograph (PPG) module attached to the underside of the device, and in direct visual contact with the skin on the chest/wrist/forehead or other location where the device adheres. The PPG module comprises of two or more light emitting diodes (LEDs), and one or more photodiodes, which measure the changes in the intensity of reflected light of one or more wavelengths. The PPG module may be capable of measuring blood oxygenation, and/or levels of Haemoglobin, and/or other blood gases, such as carbon dioxide ($CO_2$), and/or heart rate, and/or other measures derived from changes in blood flow. In various embodiments, the device uses the above-mentioned optical sensor, or a different sensor, emitting Electromagnetic waves at two or more wavelengths, to measure Blood Glucose levels.

In some embodiments of the invention, an algorithm running on the MCU of the wearable device first detects the R-peaks on each 20-sec segment of the User's ECG. After determining the R-peak using the Pan-Tompkins algorithm, the algorithm identifies the first minima after the R-peak (the S-point), and then the T-peak following it. By measuring the vertical distance between the PR-segment and the ST-segment, the algorithm determines the value of ST-depression for each 20-sec segment of ECG—internally referred to as 'Cardiac Strain'.

In some embodiments of the invention, first two ECG recordings of the User are taken—one during exercise and one during rest. These recordings are used to determine two thresholds $l_1$ and $l_2$, for ST-depression of the User, and the User is then guided through an exercise protocol, where their value of ST-depression is kept between $l_1$ and $l_2$. This is achieved by giving the User a single-vibration and prompting them to increase their exercise intensity when their value of ST-depression is going below $l_1$, and giving the User a double-vibration and prompting them to decrease their exercise intensity when their value of ST-depression is going above $l_2$. This process is continued for a period of 15-45 mins, depending on the age and general fitness level of the User, as determined from their two initial recordings.

In various embodiments, the Wearable device measures inhalation and exhalation cycles and Breathing Rate (BR) using an electrical impedance measured between two or more electrodes, and/or from the movements of the accelerometer(s), and/or from the signal measured on the PPG module, and/or from the variation in the magnitude of the R-peaks and/or variation in the RR-intervals as measured on the ECG sensor.

In various embodiments, the Wearable device, when affixed vertically or horizontally on the sternum, or any other location on the chest, uses the SCG data collected from the accelerometer, to detect cardiac events including, but not limited to: Heart murmurs, Aortic valve opening (AO), Mitral valve opening (MO), Aortic valve closure (AC), Mitral valve closure (MC), Rapid Ejection (RE), Rapid Filling (RF), and Atrial Systole (AS), the peak after the AO event on the y-axis of the SCG (J-wave).

In various embodiments, the Wearable device uses the AFE sensor to record the ECG of the User during exercise, and calculates Heart Rate and/or Heart Rate Variability and/or ST-elevation from the ECG signal. The raw ECG data, and the derived parameters are stored on the flash chip in the wearable device, and/or communicated to the gateway device (smartphone or smartwatch) using a wireless communication protocol.

In various embodiments, the wearable device uses the ECG data to record arrhythmias in the User, by measuring the regularity of the heart rate variations on the basis of the RR-intervals recorded. The algorithm used to determine whether a particular beat is arrhythmic or not is described in FIG. 4.

In various embodiments, the wearable device records the ECG, and then uses a Convolutional Neural Network based algorithm for arrhythmia detection. The Network is trained on single-lead ECG data annotated by experts earlier, and the classification object is saved on the memory of the wearable device and/or the gateway device, and then the raw ECG data recorded on the wearable device is passed to the classification object, and the classification is stored on the memory chip of the wearable device, or passed to the gateway device (smartphone or smartwatch) through a wireless communication chip.

In various embodiments, the wearable device computes the pre-ejection period (PEP) by calculating the time-delay between the R-peak of the ECG, and the Aortic valve opening (AO) peak on the SCG signal. This is stored for every beat and/or averaged for a specified length of time (2 secs to 5 mins).

In various embodiments, the wearable device computes the PEP for the User during exercise for a specified time period (5 secs to 1 min) by storing the ensemble of all the beats (200-1200 ms from the R-peaks or 10-200 ms before the R-peak of each individual beat) and then looking for the AO peak in the ensemble signal.

In various embodiments, the wearable device computes the left-ventricular ejection time (LVET) by calculating the time-delay between the Aortic valve opening (AO) peak and the Aortic valve closure (AC) peak on the SCG signal. This is stored for every beat and/or averaged for a specified length of time (2 secs to 5 mins).

In various embodiments, the wearable device computes the LVET for the User during exercise for a specified time period (5 secs to 1 min) by storing the ensemble of all the beats (200-1200 ms from the R-peaks or T-peaks of each individual beat) and then looking for the AC peak in the ensemble signal.

According to various embodiments of the present invention, the Cardiac Time Intervals described herein are used to calculate a values for Stroke Volume (SV) and Cardiac Output (CO) in the form of:

$$SV = y_1*PEP + y_2*LVET + y_3*(PEP/LVET) + y_4*amp(AO) + y_5*IHR; \text{ or}$$

$$SV = f(PEP, LVET, amp(AO), IHR); \text{ and}$$

$$CO = SV*IHR;$$

Here, the constants $y_i$ are typically regression coefficients derived from a training set consisting of a population database containing individuals in different age-groups, heights, weights, BMIs and prior medical histories, $f$ is a linear or non-linear function. IHR denotes the instantaneous Heart Rate. In various embodiments, the regression coefficients, are determined separately for different age-groups or population groups with particular heights, weights and BMIs.

In various embodiments, the wearable device computes a value of the PEP gradient ($\Delta$PEP) as:

$$\Delta PEP = PEP(t_1) \times PEP(t_2); \text{ or}$$

$$\Delta PEP = Avg(PEP(t_{1i})) - Avg(PEP(t_{2i})); \text{ or}$$

$$\Delta PEP = Median(PEP(t_{1i})) - Median(PEP(t_{2i})); \text{ or}$$

$$\Delta PEP = Slope(lsqfit(PEP(t_i))$$

Here $PEP(t_1)$ and $PEP(t_2)$ are the instantaneous PEP values on two consecutive beats, $PEP(t_{1i})$ and $PEP(t_{2i})$ are the PEP values in two consecutive intervals of time, each interval having a length of 1 sec-10 mins, the Avg is calculated after removing statistical outliers, and lsqfit(PEP(t)) is the linear least-squares fit through the PEP values measured in a time interval of length 1 sec-10 mins, after outliers have been removed.

In various embodiments, the wearable device computes a value of cardiac fatigue using the value of $\Delta$PEP described above, and measuring whether $\Delta$PEP is positive for one or more time intervals (each time interval of length 1 sec-10 mins) during exercise. When such a condition is detected, the wearable device sends an alert to the User through the vibration motor and/or an audio speaker located on the wearable device and/or the gateway device. The system may further advise the User to hydrate and/or take rest and/or lower speed depending on the value of $\Delta$PEP and the duration for which it was found to be positive.

In various embodiments, the wearable device computes a value of cardiac fatigue using the value of $\Delta$PEP described above, and measuring whether $\Delta$PEP is positive for one or more time intervals (each time interval of length 1 sec-10 mins) during exercise, when Heart Rate was either constant or increasing. When such a condition is detected, the wearable device sends an alert to the User through the vibration motor and/or an audio speaker located on the wearable device and/or the gateway device. The system may further advise the User to hydrate and/or take rest and/or lower speed depending on the value of $\Delta$PEP and the duration for which it was found to be positive.

In various embodiments, the wearable device computes a value of cardiac fatigue using the value of $\Delta$PEP described above, and measuring whether $\Delta$PEP is positive for one or more time intervals (each time interval of length 1 sec-10 mins) during exercise, when Exercise Intensity (measured by Speed or standard deviation of the Y-axis accelerometer data) was either constant or increasing. When such a condition is detected, the wearable device sends an alert to the User through the vibration motor and/or an audio speaker located on the wearable device and/or the gateway device. The system may further advise the User to hydrate and/or take rest and/or lower speed depending on the value of $\Delta$PEP and the duration for which it was found to be positive.

In various embodiments, the wearable device computes a value of the LVET gradient ($\Delta$LVET) as:

$$\Delta LVET = LVET(t_1) - LVET(t_2); \text{ or}$$

$$\Delta LVET = Avg(LVET(t_{1i})) - Avg(LVET(t_{2i})); \text{ or}$$

$$\Delta LVET = Median(LVET(t_{1i})) - Median(LVET(t_{2i})); \text{ or}$$

$$\Delta LVET = Slope(lsqfit(LVET(t_i))$$

Here $LVET(t_1)$ and $LVET(t_2)$ are the instantaneous LVET values on two consecutive beats, $LVET(t_{1i})$ and $LVET(t_{2i})$ are the LVET values in two consecutive intervals of time, each interval having a length of 1 sec-10 mins, the Avg is calculated after removing statistical outliers, and lsqfit(LVET(t_i)) is the linear least-squares fit through the LVET values measured in a time interval of length 1 sec-10 mins, after outliers have been removed.

In various embodiments, the wearable device computes a value of cardiac fatigue using the value of $\Delta$LVET described above, and measuring whether $\Delta$LVET is negative for one or more time intervals (each time interval of length 1 sec-10 mins) during exercise, while PEP has remained the same or increased. When such a condition is detected, the wearable device sends an alert to the User through the vibration motor and/or an audio speaker located on the wearable device and/or the gateway device. The system may further advise the User to hydrate and/or take rest and/or lower speed depending on the value of $\Delta$LVET and the duration for which it was found to be negative.

In various embodiments, the wearable device computes a value of cardiac fatigue using the value of $\Delta$LVET described above, and measuring whether $\Delta$LVET is negative for one or more time intervals (each time interval of length 1 sec-10 mins) during exercise, while Heart Rate has remained the same or decreased. When such a condition is detected, the wearable device sends an alert to the User through the vibration motor and/or an audio speaker located on the wearable device and/or the gateway device. The system may further advise the User to hydrate and/or take rest and/or lower speed depending on the value of $\Delta$LVET and the duration for which it was found to be negative.

In various embodiments, the wearable device is configured to send a real-time alert to the User if any cardiac fatigue and/or arrhythmia and/or abnormal ST-elevation and/or abnormal value of PEP/LVET/SV/CO are computed on the device. Such alerts are sent to the User by way of a vibration motor on the wearable device, and/or blinking of LEDs located on the wearable device, and/or a change on an electronic display on the wearable device, and/or an audio message issued through a speaker located on the wearable device.

In various embodiments, the wearable device is configured to send a real-time alert to the User if any cardiac fatigue and/or arrhythmia and/or abnormal ST-elevation and/or abnormal value of PEP/LVET/SV/CO are computed on the device. Such alerts are sent to the User by way of a message sent to the gateway device (smartphone or smartwatch) and communicated to the User by way of the vibration motor on the gateway device, and/or a notification displayed on the gateway device, and/or an audio message issued through the speaker located on the gateway device.

In various embodiments, the wearable device computes a value of Respiratory Rate (RR) in breaths per minute, by first calculating Respiratory cycles from the variation in QR-amplitudes measured from the ECG, and/or from a variation in the amplitude of the T-peak as measured in the ECG, and/or from the variation in the baseline of the ECG signal, obtained after applying a lowpass filter to the raw ECG signal with a cutoff at 1.5 Hz, and/or from the variation in the Z-axis of the accelerometer.

In various embodiments, the wearable device computes a value of Tidal Volume (TV) in ml or litres, by first calculating Respiratory cycles from the variation in QR-amplitudes measured from the ECG over a specified period of time, and then calculating the Tidal volume as:

$$TV=f(Max(QR\_amp)-Min(QR\_amp),Avg(QR\_amp),$$
$$Max(T\_amp),Min(QR\_amp))$$ where QR_amp is
the amplitude of R-peak of the ECG, measured
in millivolts, and T_amp is the amplitude of the
T-peak of the ECG, measured in millivolts.

In various embodiments, the wearable device computes a value of Minute Ventilation (VE) in liters per minute, using a combination of the Respiratory Rate (in breaths per minute) and Tidal Volume (in litres), to calculate Minute Ventilation as:

$$VE=RR\times TV$$

In various embodiments, the health monitoring system contains an elastic strap, with a pressure sensor that measures the Respiratory cycles by recording the variations in the pressure felt in the pressure sensor on the body, and/or the variations in the tension of the strap measured by a spring embedded in the elastic strap. The strap sends the signals from the pressure sensor and/or the spring to the device coupled with the strap using a wired connection and/or a wireless communication module, which computes a value of the Respiratory Rate in breaths per minute.

In various embodiments of the present invention, when the User is being monitored while running, the wearable device computes the ground contact time (GCT, in seconds or milliseconds), and/or flight time (FT, in seconds or milliseconds) and/or cadence (Cd, in steps/min). When the accelerometer is worn in a manner such that it shows a value of 1 g while the User is standing, then the GCT is computed as the value above time between the zero-crossings when the value goes from negative to positive, and then back from positive to negative on the Y-axis of the accelerometer. The FT is calculated as the time between the zero-crossings when the value goes from positive to negative, and then back from negative to positive on the Y-axis of the accelerometer. These values are computed every 1-30 seconds, and stored on the memory chip on the wearable device, and/or sent to the gateway device via a wireless communication chip.

In various embodiments of the present invention, the computing chip on the device uses the ECG signal measured on the device, to calculate a value of ST-elevation from the single-lead ECG. This value is stored in the device memory, and communicated to the mobile application and/or server using the wireless communication ship.

In various embodiments of the present invention, a cardiac health index is calculated by calculating the value of the slope of the ST-elevation Vs Heart Rate during some portion of the User's exercise session. A higher value of the slope indicates worse Cardiac Health.

In various embodiments of the present invention, a cardiac health index is calculated by calculating the value of the ratio of Max(ST-elevation)/Max(HR) over some portion of the User's exercise session.

In various embodiments of the present invention, a cardiac health index is calculated by calculating the value of the area under the Hysteresis curve when ST-elevation is plotted against Heart Rate for a User's exercise session.

In various embodiments of the present invention, a cardiac health index is calculated by calculating the Maximum or Average value of ST-elevation in a pre-determined Heart Rate range, which depends on the particular exercise that the User is doing, and/or their age.

In various embodiments, the exercise health monitoring system uses the Heart Rate, PEP, LVET, Cadence, GCT, FT, Speed values from the User's data during a run, to compute the Optimal Cadence, GCT and FT value ranges corresponding to each particular speed that the User ran at, by calculating the cadence, GCT and FT values corresponding to each speed, where Heart Rate is minimal and/or PEP is maximum within the normal range, and/or LVET is maximum within the normal range, and/or the value of 'Cardiac fatigue' is the lowest. These values are communicated to the User to guide them towards the optimal running cadence and style.

In various embodiments of the present invention, the readings from a gyroscope and/or magnetometer included in the device, are used to estimate the angle of the device with the ground that the User is running on, to correctly calculate the timepoint at which the User's foot touches the ground, and therefore to calculate a more accurate value of GCT and Flight time, and thereby a more accurate value of Speed, using the procedure described above.

In various embodiments of the present invention, the speed of a User while running is determined by first calculating the point in time to at which the acceleration in the Y-axis crosses 1 g, or where the velocity in the Y-axis crosses 0, and taking another timepoint $t_i$, in the 10-100 ms range preceding to, where the velocity in the Z-axis at time $t_i$, $V_z(t_i)$ is determined as:

$$V_z(t_i)=\int_{t0}^{ti}a_y dtf/(2*\int_{t0}^{ti}a_z dt)+(\int_{t0}^{t0}a_y dt)/2$$

This procedure is repeated to calculate the velocity at multiple timepoints $t_i$, and therefore obtain a more accurate estimate of the velocity of the runner in the forward direction ($V_z$) at different time points. Once the velocity at any timepoint $t_i$ is determined, the velocity at other timepoint $t_s$ in any continuous section of data is calculated by integrating the acceleration between the two timepoints as:

$$V_z(t_s)=V_z(t_i)+\int_{ts}^{ti}a_z dt$$

In various embodiments of the present invention, the readings from a gyroscope and/or magnetometer included in the device, are used to estimate the angle of the device with the ground that the User is running on, to correctly calculate the timepoint (to) at which the Users velocity along the vertical direction ($V_y$) is 0, and this is used to calculate the speed at any preceding point $t_i$, within 1-100 ms of to as described above.

In various embodiments, the wearable device includes a GPS chip, capable of determining the exact position of the User during exercise or a run, and at the end of the exercise session/run, show how the various cardiac and musculoskeletal parameters including but not limited to: HR, PEP, LVET, SV, CO, Shock, Cadence, Speed, Braking force, Sway: varied at different points of the route traversed by the User.

In various embodiments, the wearable device worn on the chest of the User includes a Barometer chip, which is capable of measuring the altitude of the User with respect to the sea level, and record changes in the altitude of the User with time.

In various embodiments, the exercise health monitoring system calculates a value for the Power with which the person is running (in Watts), using the measured values of GCT, Flight Time, Cadence, Maximal Acceleration in the Y and Z directions, rate of change of elevation (inclination), height and weight of the User. In other words, the Power (P) of the User is measured in Watts as follows:

$$P=f(GCT,FT,Cd,Max_z,Max_y,Inclination,Weight,Height)$$

In various embodiments, the wearable device computes a value of the Lactate Threshold (LT) and/or Ventilatory Threshold (VT) and/or Anaerobic Threshold (AT), by calculating the speed (in km/hr or m/sec) or pace (in seconds/ km or seconds/mile) at which the Runner's Respiratory Rate suddenly starts increasing in a non-linear fashion with respect to pace and/or speed and/or Heart Rate and/or Power. VT is calculated to be the pace or speed at which the slope of the graph of RR vs Pace and/or RR vs HR and/or RR vs Power suddenly increases, after a linear increase over some period of time.

In various embodiments, the wearable device computes a value of the Lactate Threshold (LT) and/or Ventilatory Threshold (VT) and/or Anaerobic Threshold (AT), by calculating the speed (in km/hr or m/sec) or pace (in seconds/ km or seconds/mile) at which the Runner's Minute Ventilation (VE) suddenly starts increasing in a non-linear fashion with respect to pace and/or speed and/or Heart Rate and/or Power. VT is calculated to be the pace or speed at which the slope of the graph of VE vs Pace and/or VE vs HR and/or VE vs Power suddenly increases, after a linear increase over some period of time.

In various embodiments, the exercise health monitoring system calculates values for RR, TV, VE, HR, Speed and Power for the runner in real-time, and guides a runner to run in their optimal zone, which is just below their Anaerobic Threshold or Ventilatory Threshold. The exercise health monitoring system does this by alerting the runner with a vibration and/or audio message, when they are approaching their Anaerobic Threshold or Ventilatory Threshold, and giving the runner a second longer vibration or different audio alert when they are in danger of crossing this AT/VT. Thus, until the runner receives the first alert, he/she knows they can exert themselves further, and if they receive the second alert, they know they need to slow down.

In various embodiments, the exercise health monitoring system consists of two wearable devices embedded in the soles of the left and right shoe of the User, each consisting of an accelerometer, and one or more of the following: a wireless communication chip, a battery, a computing device, a vibration motor, an energy harvesting circuit capable of harvesting energy from the pressure of the foot and charging the battery. These two wearable devices embedded in the shoes connect with a gateway device (smartphone or smartwatch), and compute one or more of the following parameters: cadence, speed, shock, braking, GCT, FT; and issuing alerts to the User by way of a vibration and/or messages sent to the gateway device during exercise/running. The wearable devices situated in the shoes are capable of recharging their batteries from the energy harvested from foot strikes, i.e. when the user's foot lands on the ground or other underlying surface.

In various embodiments, the exercise health monitoring system consists of one or more wearable devices worn on the chest or feet of the User, and a wireless headphone/earphone system worn by the User. This system is capable of measuring cardiac and musculoskeletal parameters including but not limited to: HR, PEP, LVET, SV, CO, Cardiac Fatigue, Shock, Cadence, Braking force, Sway; and sending real-time alerts to the User by way of vibrations and/or audio messages sent directly to the wireless headphones using a wireless communication protocol, without the use of any other gateway device. These alerts are played directly into the User's ears during exercise/running so that they can be alerted to different kinds of conditions.

In various embodiments, the User can wear one or more Wearable devices, which connect with a single gateway device such as a smart phone/smart watch/router wirelessly, using a wireless communication protocol such as Bluetooth or Wi-Fi. The Wearables first sync their internal clocks with the real time clock (RTC) of the gateway device—smartphone/smart watch, other gateway device—so that the internal clocks of the Wearables are aligned with the clock of the gateway device, as well as with each other. This synchronization is achieved by the smart phone sending its exact UTC time to the Wearables via Bluetooth, or some other wireless communication protocol, and the Wearables then updating their RTC to this exact time (to a resolution of milliseconds), plus a delta which has been calculated previously, and which is the time delay between the sending of the Bluetooth Low Energy (BLE) packet by the smart phone, and the updating of the RTC on the Wearable. This process of synchronization is optionally repeated every 1 hour or as needed, so that any drift between the clocks of different Wearables is normalized every 1 hour.

In various embodiments, the Wearable(s) transfer data to the smart phone/smart watch or other gateway device wirelessly via Bluetooth or some other near field communication (NFC) protocol, and then from there the data is transferred to a web client via Wi-Fi, and stored in a secure database on a web server. In another embodiment, the data is transferred directly from the Wearable to the web using Wi-Fi or 3G/4G wireless communication. This data can then be accessed by doctors or caregivers or the User themselves, using a web application, and historical data for each patient can be viewed and analysed.

In various embodiments, the data stored on the web for multiple Users, is used in Machine learning algorithms such as a convolutional neural networks and/or Bayesian Classifiers and/or support vector machines, to distinguish between healthy and pathological conditions of the User in question, by using the stored and annotated data as a training set, and applying the classification algorithms on the User's data in real-time on the MCU of the wearable device or the gateway device, while it is connected to the wearable device over Bluetooth.

In various embodiments, the Wearable device records the ECG data at a frequency of anywhere between 125 Hz and 4 kHz, Accelerometer data at a frequency of anywhere between 5 Hz and 2 kHz, and sends the data to the MCU, where the data is processed using mean/median/Band pass filters, and automated peak detection algorithms annotate each signal, and calculate the timing of the electrical, mechanical and blood-flow related events in the cardiac cycle.

In various embodiments, the pre-ejection period (PEP) is measured indirectly by calculating the time interval between the R-wave on the ECG and the J-wave, where the J-wave is assumed to be the highest maxima following the R-peak of the ECG, between 10-140 milliseconds after the R-peak of the ECG, in the y-axis data of the accelerometer, after removal of motion artifacts ($R-J_{interval}$). The equation used to derive PEP is of the form:

$$PEP = x_1 * R - J_{interval};$$

where the constant $x_1$ determined independently from his/her data, or from a population database.

According to another embodiment of the present invention, the pre-ejection period (PEP) is calculated before and during exercise being conducted by the User, and as the User is exercising, assuming that the User starts from rest at time $t_1$, the change in PEP due to exercise is calculated as:

$$\Delta PEP = PEP_{t2} - PEP_{t1}$$

Simultaneously, the power for any period of time $\Delta t = t_2 - t_1$, is calculated as: $P = F \cdot S / \Delta t$. The power (P), and the pre-ejection period (PEP) is calculated for every 10 sec interval, and the change in power ($\Delta$P) and change in PEP ($\Delta$PEP) is calculated between every two successive intervals. Then a value known as the Exercise PEP Index (EPEPI), is calculated as:

$$EPEPI = \Delta P^* \Delta PEP.$$

In various embodiments, the Wearable device records the ECG data as described above, and uses an algorithm running on the MCU, which uses the 3-10 data points around the P/Q/R/S/T peak, and then uses wavelet transforms or other peak-interpolation techniques to further improve the accuracy of the detected peaks to less than 1 millisecond.

According to various embodiments, the Wearable device uses data from the ECG sensor, PPG sensor, and the SCG as measured from the accelerometer, as described herein, and when the Wearable device is affixed on some part of the chest, to calculate values for the cardiac time intervals (CTIs) including, but not limited to: Pre-ejection period (PEP), left ventricular ejection time (LVET), Q-wave of ECG to the first sound from the Phonocardiogram (QS1), Q-wave of ECG to the second sound from the Phonocardiogram (QS2), first sound to second sound of Phonocardiogram (S1S2), PR-interval from ECG, QRS duration from ECG, the time interval between the R-wave on the ECG, the J-wave on the y-axis of the SCG (R-J interval), Systolic Time, Diastolic Time, $PTT_{foot}$, $PTT_{peak}$, Electro-mechanical Activation time (R-peak to MC), Isovolumetric Relaxation Time (IVRT), which is the time interval from AC to MO on the Seismocardiogram, and Isovolumetric Contraction Time (IVCT), which is the time interval from MC to AO, and/or the like.

In other embodiments of the invention, the values mentioned in [39] above are used to calculate the Tei index, or the Myocardial Performance Index, as MPI=(IVRT+IVCT)/LVET. This value is calculated for some or every heartbeat on the Wearable device, and is sent to the accompanying smart phone or other gateway device via Bluetooth, or some other NFC protocol.

DETAILED DESCRIPTION OF THE DRAWINGS

FIG. 1 shows a schematic layout of the Wearable Device, and shows a plurality of sensors including an ECG sensor (1), accelerometer (2), that record data, and send the data to a microcontroller or microprocessor or another computing device (3) on the Wearable device, which stores the ECG data in the internal Flash memory (4) and communicates the derived parameters to the User through the Wireless Communication module (5) to the User's mobile application (7). The MCU is also able to alert the User under various conditions by sending tactile feedback to the User through the vibration motor (6).

FIG. 2 shows the process followed to initiate the protocol for Ischemic Pre-conditioning for a new User. The User first takes one recording at rest, and one during exercise (1), to provide initial data to the system for determining the thresholds for Cardiac Strain to be used during the protocol for Ischemic Pre-conditioning (2). Once the thresholds $l_1$ and $l_2$ have been determined, the User is asked to set a lower limit alert for Cardiac Strain with a threshold of $l_1$, and an upper limit alert with a threshold of $l_2$ (3). After this the User starts a recording and follows the instructions provided in the mobile application (4), receiving vibration alerts every 20 seconds, which tell the User whether to increase or decrease their intensity of exercise (5).

FIG. 3 shows the process followed during a session of Ischemic Pre-conditioning. During one session of IPC, the User (1) wears the device and starts a recording. The ECG sensor in the wearable device measures the User's ECG (2). The ECG is analysed and a value of Cardiac Strain is calculated by the MCU (3), which then passes on the value of Cardiac Strain to an algorithm (4). Based on the thresholds determined for the User, and the value of Cardiac Strain measured for them, and the amount of time elapsed, the User either receives a single vibration (5) which prompts them to continue their exercise, or the User receives a double vibration (6), which prompts them to slow down or end their exercise session.

ADVANTAGES OF THE INVENTION

The present invention enables the continuous monitoring of various health parameters, particularly cardiac health parameters, over long periods of time due to the use of a wearable device that can be affixed to the body for long periods of time.

The present invention enables monitoring of health parameters in a fully mobile setting, hence allowing subjects to be monitored during exercise or a run covering large distances.

The present invention includes a wearable device that is capable of processing data streams being received from various sensors, and is further capable of computing derived health parameters on the device itself.

The present invention allows the User to be alerted discreetly using a vibration motor and/or an audio speaker whenever the calculated health parameters are found to be outside the normal range of values to be expected from that parameter.

The present invention allows the Users health parameters to be sent to an application running on the smart phone/smart watch or other gateway device, and also allows the data to be stored in a secure web location, so that the data can be viewed and analysed by health professionals at a later stage.

The foregoing description of the specific embodiments will so fully reveal the general nature of the embodiments herein that others can, by applying current knowledge, readily modify and/or adapt for various applications such as specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments herein have been described in terms of preferred embodiments, those skilled in the art will recognize that the embodiments herein can be practiced with modifications. However, all such modifications are deemed to be within the scope of the claims.

What is claimed is:

1. A wearable device configured to be affixed to a body of a user for ischemic pre-conditioning (IPC) of the user, the wearable device comprising:

a plurality of physiological sensors, including an ECG sensor and at least one of a skin impedance sensor; a PPG sensor; an accelerometer; and a temperature sensor;

a vibration motor; and a computing device configured to record data from any subset of the sensors, said computing device further configured to execute an IPC protocol, the IPC protocol comprising computer-readable instructions to repeatedly:

determine one or more cardiac health parameters from the plurality of physiological sensors in substantially real-time, including a value of ST-depression for a predetermined time period of an ECG signal, access first or second thresholds of the one or more cardiac health parameters, including at least ST-depression, which respectively define lower and upper limits of cardiac strain for the user during IPC, compare, in substantially real-time, one or more respective real-time cardiac health parameters, including at least ST-depression, to respective first or second thresholds, and generate an alert signal based on the comparison of the real-time cardiac health parameters to the first or second thresholds, wherein the computing device is operable to activate the vibration motor based upon the generated alert signal to provide a tactile output corresponding to an increase, a maintaining, or a decrease of an exercise level, so as to guide the user through IPC based on cardiac strain at varying exercise levels.

2. The wearable device of claim 1, further including LEDs and/or an audio speaker that provide real-time alerts to the user during exercise or resting states.

3. The wearable device of claim 1 further including a chest strap or a disposable sticker that allows the wearable device to be affixed to some part of the user's chest, wherein the plurality of physiological sensors are configured to record signals including ECG and accelerometer waveforms.

4. The wearable device of claim 1 further comprising one or more printed circuit boards (PCBs), wherein one of the PCBs further includes one or more of the following:

a USB port;

a gyroscope;

a magnetometer;

a barometer;

a battery;

a temperature sensor;

a GPS chip;

one or more LEDs;

a thermoelectric or photoelectric panel for harvesting energy from the body heat, or from light or heat in the environment;

an ultrasound transducer, configured for recording an ultrasound signal;

an electronic display; and a wireless charging coil.

5. The wearable device of claim 1, wherein the computing device is further configured to measure ECG and SCG waveforms in parallel, when affixed to the chest of the user with a strap or adhesive sticker, and further configured to derive cardiac health parameters of the individual, including one or more of the following: heart rate, respiratory rate, tidal volume, minute ventilation, arrhythmias, heart murmurs, systolic time intervals (PEP, LVET, IVRT, IVCT), left ventricular ejection fraction (LVEF), cardiac output and stroke volume, PQ-interval, ST-interval, ST-elevation, running speed, and running power.

6. The wearable device of claim 1, wherein the computing device is configured to record the accelerometer data, and to calculate the exact timing of the zero crossings in the Y-axis data of the accelerometer, and thereby a value for one or more of the following when the user is undergoing exercise, or is running: cadence (in steps per min), shock on the knees/spine (in g/sec), braking force (in g), braking velocity (in m/see or km/hr), bounce (in cms), sway (in cms or degrees from the vertical), ground contact time (in see/ms), flight time (in see/ms), and speed (in m/see or km/hr).

7. The wearable device of claim 6, wherein the computing device is configured to measure a shock value by computing the maximal slope of the Y-axis data of the accelerometer in the 1-100 ms time interval range immediately after a foot strike, and send an alert to the user when their shock value crosses a certain pre-specified threshold, through the vibration motor, and/or a message displayed on a display included in the wearable device, and/or an audio speaker located on the wearable device, and/or a message sent to a gateway device.

8. The wearable device of claim 1, further including a wireless connection to a smartphone or computing device with a display and/or speaker, which receives data wirelessly from the wearable device, and guides the user through the protocol for IPC with instructions given through text or audio/visual medium.

9. The wearable device of claim 1, further comprising a smartphone or a computer including a video camera, which receives data from the wearable device, and further processes the video recording of the user in substantially real-time, to give recommendations on how to modify an exercise protocol being followed for the IPC session.

10. The wearable device of claim 1, wherein the wearable device is operable to communicate data with a gateway device, the gateway device comprising a smartphone, smartwatch, or router.

11. The wearable device of claim 1, wherein the predefined time period is substantially equivalent to 20 seconds.

12. The wearable device of claim 1, further comprising a wireless communication chip that sends data to a gateway device, wherein the gateway device comprises a smartphone or smartwatch or router.

13. The wearable device of claim 1, wherein said first and second thresholds of the one or more cardiac health parameters, including ST-depression, are predetermined from a rest state and an exercise state of the user.

14. The wearable device of claim 1, wherein IPC protocol provides an activation of the vibration motor to alert the user to increase their exercise level if the real-time value of the one or more cardiac health parameters, including at least ST-depression, is below the first threshold.

15. The wearable device of claim 1, wherein the IPC protocol provides an activation of the vibration motor to alert the user to maintain their exercise level if the real-time value of the one or more cardiac health parameters, including at least ST-depression, is between the first and second thresholds.

16. The wearable device of claim 1, wherein the IPC protocol provides an activation of the vibration motor to alert the user to decrease their exercise level if the real-time value of the one or more cardiac health parameters, including at least ST-depression, is above the second threshold.

17. The wearable device of claim 1, the tactile output including one of two or more unique tactile outputs.

18. The wearable device of claim 17, the two or more unique tactile outputs including a first tactile output and a different, second tactile output.

19. A system for monitoring the health of a human user in a mobile setting, the system comprising:

one or more PCBs including an ECG sensor; a computing device configured to record data from the ECG sensor, flash memory, and a wireless communication module operable to communicate wirelessly with a gateway device;

the one or more PCBs being affixed to a chest strap or clothing so as to maintain the one or more PCBs near the user's chest; and the one or more PCBs or gateway device further including one or more of a vibration motor for tactile outputs, a speaker or headphone interface for auditory outputs, and a display or one or more LEDs for visual outputs;

wherein the system is operable to, by the computing device or gateway device, execute computer-readable instructions of an IPC protocol, the IPC protocol operable to repeatedly:

process ECG signals in substantially real-time to calculate a value of ST-depression for a predetermined time period of an ECG signal, access, from the flash memory or gateway device, first or second thresholds of ST-depression respectively defining the lower and upper limits of cardiac strain for the user during IPC, compare the real-time value of ST-depression to the first or second thresholds, and generate an alert signal based on the comparison of the real-time value of ST-depression to the first or second thresholds, wherein the computing device is operable to produce a tactile, auditory, and/or visual output, based upon the generated alert signal, corresponding to an increase, a maintaining, or a decrease of an exercise level, so as to guide the user through IPC based on cardiac strain at varying exercise levels.

20. The system of claim 19, wherein the PCB or chest strap or clothing further includes one or more of the following:

a PPG sensor;

an accelerometer;

a port for charging the system;

a gyroscope;

a magnetometer;

a barometer;

a battery;

a temperature sensor;

a GPS chip;

a pressure sensor to measure pressure between the chest strap and the user's chest;

a strain sensor to measure the strain in the chest strap or shirt or vest when it is worn by the user;

a thermoelectric or photoelectric panel for harvesting energy from body heat, from motion, or from light/heat in the environment;

an ultrasound transducer, configured for recording an ultrasound signal; and a wireless charging coil.

21. The system of claim 19, where the wireless communication module sends data to a gateway device, which displays the parameters calculated by a computing element housed within the device, and which can be used to configure the wearable device for different functions.

22. The system of claim 21, wherein the gateway device comprises a smartphone, smartwatch, or router.

23. The system of claim 19, wherein the chest strap or clothing includes an array of electrical sensors configured to record multi-channel ECG waveforms and/or impedance, and to measure one or more of the following: respiratory rate, tidal volume, VO2 max, fluid content in the lungs, ST-elevation, left ventricular ejection fraction, stroke volume, cardiac output, and galvanic skin response.

24. The system of claim 19, further configured to compute a value for the ventilatory threshold or lactate threshold for a user during exercise, by estimating the exercise intensity level at which the user's respiratory rate or minute ventilation starts increasing non-linearly with respect to exercise intensity level and/or heart rate and/or power for a certain period of time, and to alert the user through a vibration, a message displayed on an electronic display included in the device, and/or an audio message whenever the user is close to said threshold, thereby enabling the user to run in a zone close to their anaerobic threshold.

25. The system of claim 19, wherein said first and second thresholds of ST-depression are predetermined from a rest state and an exercise state of the user.

26. The system of claim 19, wherein the system is further operable to measure one or more of the following parameters: PEP, LVET, HR, respiratory rate, tidal volume, cadence, braking force, braking velocity, bounce, shock, and sway.

27. The system of claim 19, wherein the protocol provides an alert to prompt the user to increase their exercise level if the real-time value of ST-depression is below the first threshold.

28. The system of claim 19, wherein the IPC protocol provides an alert to prompt the user to maintain their exercise level if the real-time value of ST-depression is between the first and second thresholds.

29. The system of claim 19, wherein the IPC protocol provides an alert to prompt the user to decrease their exercise level if the real-time value of ST-depression is above the second threshold.

30. The system of claim 19, the tactile, auditory, and/or visual output including:

one of two or more unique tactile outputs;

one of two or more unique auditory outputs; and/or one of two or more unique visual outputs.

* * * * *